(12) United States Patent
Kotler

(10) Patent No.: US 8,092,478 B2
(45) Date of Patent: Jan. 10, 2012

(54) DEVICE AND METHOD FOR MAINTAINING UNOBSTRUCTED NASAL PASSAGEWAYS AFTER NASAL SURGERY

(76) Inventor: Robert Kotler, Beverly Hills, CA (US)

(*) Notice: Subject to any disclaimer, the term of this patent is extended or adjusted under 35 U.S.C. 154(b) by 764 days.

(21) Appl. No.: 12/080,145

(22) Filed: Apr. 1, 2008

(65) Prior Publication Data

US 2009/0248057 A1    Oct. 1, 2009

(51) Int. Cl.
*A61M 29/00* (2006.01)

(52) U.S. Cl. ......................................................... 606/191

(58) Field of Classification Search .................. 606/108, 606/191, 196, 199; 128/207.18, 200.24, 128/200.26, 203.22, 206.11, 207.13; 604/540, 604/541
See application file for complete search history.

(56) References Cited

U.S. PATENT DOCUMENTS

| | | | |
|---|---|---|---|
| 1,256,188 A | | 2/1918 | Wilson |
| 2,215,126 A | * | 9/1940 | McMillin ...................... 606/196 |
| 2,265,387 A | * | 12/1941 | McMillin ................. 128/207.18 |
| 2,569,743 A | | 10/1951 | Carlock |
| 2,672,138 A | | 3/1954 | Carlock |
| 3,049,125 A | * | 8/1962 | Kriwkowitsch ............. 606/196 |
| 3,424,152 A | | 1/1969 | Kuhlman |
| 3,682,171 A | * | 8/1972 | Dali et al. ................ 128/207.18 |
| 3,814,103 A | * | 6/1974 | Fettel et al. .............. 128/207.18 |
| 3,935,859 A | | 2/1976 | Doyle |
| 4,136,678 A | * | 1/1979 | Beach ............................. 604/19 |
| 4,221,217 A | | 9/1980 | Amezcua |
| 4,821,715 A | * | 4/1989 | Downing ................. 128/207.18 |
| 4,950,280 A | | 8/1990 | Brennan |
| 5,167,220 A | * | 12/1992 | Brown ......................... 600/157 |
| 5,185,005 A | | 2/1993 | Ballantyne |
| 5,533,506 A | * | 7/1996 | Wood ....................... 128/207.18 |
| D406,888 S | | 3/1999 | Doyle |

(Continued)

FOREIGN PATENT DOCUMENTS

EP        0 153 132 A    8/1985

(Continued)

OTHER PUBLICATIONS

Singh et al British Jornal of Anaesthesia 91 (5) 667-71 (2003).*

(Continued)

*Primary Examiner* — Gary Jackson
*Assistant Examiner* — Amy Shipley
(74) *Attorney, Agent, or Firm* — Brinks Hofer Gilson & Lione

(57) ABSTRACT

Methods and devices for maintaining nasal passages open after nasal surgery are provided. In some embodiments, the method of the present invention includes initially cleaning at least some of the bodily fluids from the nasal passages of a patient after the nasal surgery; providing a post-operative device having a first tubular member with a first proximal end and a first distal end, and a second tubular member with a second proximal end and a second distal end, where the first proximal end is connected to the second proximal end with a bridging member, and the post-operative device is splintless; inserting the first distal end and the second distal end into the nasal passages of the patient to a location where the first proximal end and the second proximal end each protrude beyond the nostril opening of the patient; and placing a packing material at least partially around each tubular member. In some embodiments of the present invention, a specialized speculum is provided to facilitate placing packing material around the tubular members of the medical device. Medical kits for use following nasal surgery are also provided.

20 Claims, 8 Drawing Sheets

U.S. PATENT DOCUMENTS

| | | | |
|---|---|---|---|
| 5,931,852 A | 8/1999 | Brennan | |
| 6,564,800 B1 | 5/2003 | Olivares | |
| 6,606,995 B1 * | 8/2003 | Sadek et al. | 128/207.18 |
| 6,772,761 B1 | 8/2004 | Rucker, Jr. | |
| 6,860,270 B2 * | 3/2005 | Sniadach | 128/207.14 |
| 6,978,781 B1 | 12/2005 | Jordan | |
| 2003/0024530 A1 * | 2/2003 | Sniadach | 128/202.28 |
| 2008/0110467 A1 * | 5/2008 | Deshpande | 128/207.14 |

FOREIGN PATENT DOCUMENTS

| | | |
|---|---|---|
| EP | 0153132 | 8/1985 |

OTHER PUBLICATIONS

Stammberger et al Eur Arch Otorhinolaryngol (1990) 247: 63-76.*

J Jones Anaesthesia 2007 62 pages 1190-1191.*

Dou et al J Neurosurg 108 164-169, 2008.*

Nakano et al Am J Respir Crit Care Med vol. 162 pp. 1102-1108, 2000.*

Piepho et al British Journal of Anaesthesia 94 (6) 859-60 (2005).*

Kuner et al Dis Chest 1967, 51, 270-274.*

Shoenfeld et al AJR 138: 972 May 1982.*

Berthelsen et al Anesthesiology 63:457-458, 1985.*

Gujrathi et al International Journal of Pediatric Otorhinolaryngology (2004) 68, 399-407.*

Couldwell Journal of Neuro-Oncology 69 237-256, 2004.*

Kawamura et al "Rapid Long Tube Intubation of the Jejunum—An Improved Technique" Japanese Journal of Surgery vol. 14 No. 4 pp. 299-3C4, 1984.*

PCT International Search Report from PCT/US2009/038985, 2009.

Skolnik, M.D. et al.; "Choanal Atresia"; Symposium on the Nasal Cavities; The Otolaryngologic Clinics of North America, vol. 6, No. 3; Oct. 1973; 9 pages.

Non-final Office Action mailed Jun. 23, 2011 for U.S. Appl. No. 12/482,235.

Peck, George, MD, *Techniques in Aesthetic Rhinoplasty*, Thieme-Stratton, Inc. publisher, New York, NY, 1984, p. 109.

Shippert Medical Technologies Corporation catalog, *Leading Edge Technology and Solutions for the Medical Professional*, 2002-2003, 80 pages.

Kotler, Robert, MD, *Secrets of a Beverly Hills Cosmetic Surgeon, The Expert's Guide to Safe, Successful Surgery*, Ernest Mitchell publisher, Beverly Hills, CA, 2003, pp. 139-155, 198-200, 220.

Boston Medical Products, Nasal Splints, Doyle Open Lumen Splint, 2006, http://www.bosmed.com/nasal/openlumen.html, last printed Mar. 31, 2008, 2 pages.

Netter, Frank, MD, *Atlas of Human Anatomy, 4th Edition*, Saunders Elsivier publisher, Philadelphia, PA, 2006, plate 37 (Speculum view), 1 page.

The Medical Supply Company, Inc., 60cc Irrigation Syringes with Tip—KND67000 from TMSC, http://www.medsupplyco.com/Products/ProductDetails.cfm?ProductNumber=KND67000#, last printed Oct. 19, 2007, 1 page.

Medtronic, Nasal Silicone Airway Tube, Dec. 31, 2003, http://www.xomcat.com/index.php?zone=both&cat=5&sub=67&prodline=834, last printed Jun. 16, 2008, 1 page.

Enk, Dietmar, MD, et al., "Nasotracheal Intubation: A Simple and Effective Technique to Reduce Nasopharyngeal Trauma and Tube Contamination" *Anesth. Analg.*, vol. 95, pp. 1432-1436 (2002), available at http://www.anesthesia-analgesia.org/cgi/content/full/95/5/1432, last printed Mar. 5, 2009, 9 pages.

Breeze Nasal Airway Splint, Micromedics Advertisement, 1 page, Oct. 2008.

Portex, Airway—Nasopharyngeal (Non USA) from http://www.smiths-medical.com/catalog/airways/nasal-airways/airway-nasopharyngeal.html, last printed Mar. 5, 2009, 1 page.

\* cited by examiner

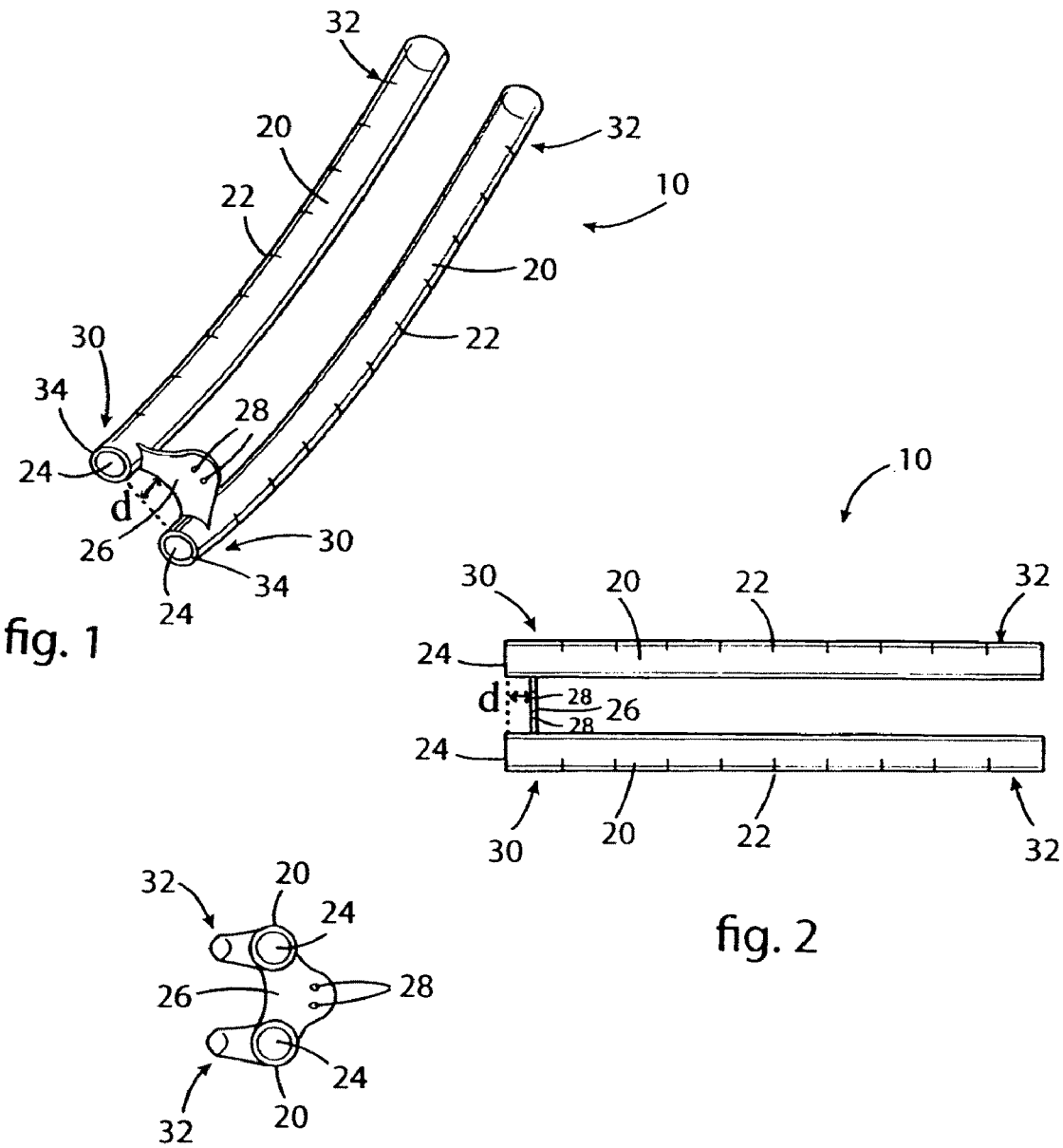

DEVICE AND METHOD FOR MAINTAINING UNOBSTRUCTED NASAL PASSAGEWAYS AFTER NASAL SURGERY

FIELD OF THE INVENTION

The present invention relates generally to medical devices and methods, and more particularly, to medical devices and methods for use after nasal surgery.

BACKGROUND OF THE INVENTION

Nasal surgery may be performed for purposes such as appearance enhancement, reconstruction following an injury, or breathing improvement. Following nasal surgery, it is typically necessary to place packing into the nasal cavity upon the conclusion of the surgery. Such packing may be used to temporarily maintain nasal components in their proper and anatomically correct positions after any manipulation, repositioning, and/or reconstruction that took place during the surgery, while nature begins the healing and repair process.

Nasal packing may also be used following nasal surgery to reduce the chance of bleeding, by prophylactically tamponading the nasal structures most likely to be the source of bleeding, such as the interior of the nose which contains a plurality of blood vessels. Bleeding after nasal surgery can be fatal or result in the loss of a considerable amount of blood and cause serious complications.

Post-operative nasal packing may be required for up to five days after nasal surgery. For most patients, any pain following the surgery may be controlled with medication and is secondary to the essentially complete nasal obstruction caused by the packing material. The packing makes mouth breathing obligatory and can cause a dry throat and extreme discomfort for the patient. In addition, the patient's sense of smell, which may be critical to the enjoyment of food, may be compromised. All of this often creates a frightened and anxious patient.

The reported extreme discomfort and the above other significant dissatisfactions caused by the current, requisite full post-operative nasal packing has caused potential patients to forego life-changing nasal surgery that would otherwise have been successful in improving allergy symptoms, improving smell and taste, preventing significant complications such as sinus infections, improving appearance, and/or preventing snoring, for example. Prior attempts to address such problems include the use of a nasal splint with integral, partial breathing passages, such as the splint disclosed in U.S. Pat. No. 3,935,859 to Doyle, where the purpose of the splint is to stabilize the repaired nasal septum. Such devices do not contain full breathing tubes, nor do they include breathing tubes that are amenable to easy cleaning by the patient, as the tubes reside entirely within the nasal passages. Experience has shown that such devices quickly become obstructed and, without proper medical attention, the blockage cannot be relieved.

Prior attempts to maintain open nasal passageways after surgery include embedding an airway within a pre-formed packing material. Such devices are limited to use with only the type, size, and configuration of packing material supplied with the device and cannot be modified based upon the preferences of the physician or the patient. Further, such devices do not allow for easy cleaning of the airway by the patient and therefore, cause patient discomfort as a result of obstruction of the airway.

Other attempts have been made to develop devices for insertion into the nasal passages, where the devices are designed to prevent snoring. Such devices are not designed for post-operative use. For example, several of these devices exert pressure against the inner walls of the nasal passages, which may be damaging to the delicate nasal architecture after surgery. In addition, because such devices are not designed for use after surgery, they do not address the problem of obstruction caused by accumulating blood and other bodily fluids following nasal surgery.

Therefore, what is needed are devices and methods that allow the advantages of complete nasal packing following surgery without totally obstructing the nasal passages of a patient and compromising the patient's ability to breathe normally, and without causing damage to the delicate nasal architecture following nasal surgery.

SUMMARY OF THE INVENTION

In some embodiments of the present invention, a method for maintaining nasal passages open after nasal surgery is provided. The method may include: initially cleaning at least some of the bodily fluids from the nasal passages after nasal surgery; providing a post-operative device having a first tubular member with a first proximal end and a first distal end, and a second tubular member with a second proximal end and a second distal end, where the first proximal end is connected to the second proximal end with a bridging member, and the post-operative device is splintless; inserting the first distal end and the second distal end into the nasal passages of the patient to a location where the first proximal end and the second proximal end each protrude beyond the nostril opening of the patient; and at least partially surrounding each tubular member with packing material. In some embodiments, prior to the placement of the packing material, the bridging member is secured to the columella of the patient using sutures, for example, to prevent displacement. The first proximal end may be connected to the second proximal end either before or after the first distal end and the second distal end are inserted into the nasal passages. In other embodiments, a single-unit medical device is used, and no connection is necessary.

In certain embodiments, the method of the present invention includes cleaning each tubular member with a fluid-containing syringe, which may include an adapter to removably connect the syringe to each tubular member. In some embodiments, the method includes measuring the length of the nasal floor of a patient and trimming the first distal end and the second distal end, based on the result of the measuring, prior to securing the post-operative device.

In some embodiments of the present invention, a specialized speculum is provided to facilitate placing packing material at least partially around the tubular members of a post-operative medical device. The speculum may include two leg members, where one leg member includes an engagement member configured to coincide with the tubular member and permit the medical professional to exert pressure against the tubular member to thereby increase the space between the tubular member and the inner portion of the nostril and facilitate insertion of packing material into the nasal cavity using forceps or another suitable medical instrument.

In other embodiments of the present invention, a medical kit for use following nasal surgery is provided. The medical kit may include a post-operative medical device having a first tubular member with a first proximal end and a first distal end, and a second tubular member with a second proximal end and a second distal end, where the first proximal end is connected to the second proximal end with a bridging member, and the post-operative device is splintless; an insertion speculum adapted to at least partially surround and mate with the post-operative medical device; and a syringe for cleaning the tubular members of the medical device. The medical kit may also include a packing material and/or a measuring device configured to measure the length of the nasal floor of a patient.

Other features and advantages of the present invention will be apparent from the following detailed description of exemplary embodiments, taken in conjunction with the accompanying drawings which illustrate, by way of example, the principles of the invention.

BRIEF DESCRIPTION OF THE DRAWINGS

FIG. 1 is a perspective view of one embodiment of a post-operative medical device of the present invention;

FIG. 2 is a top view of the post-operative medical device of FIG. 1;

FIG. 3 is a front view of the post-operative medical device of FIG. 1;

Wherever possible, the same reference numbers will be used throughout the drawings to refer to the same or like parts.

DETAILED DESCRIPTION

Figure 4:
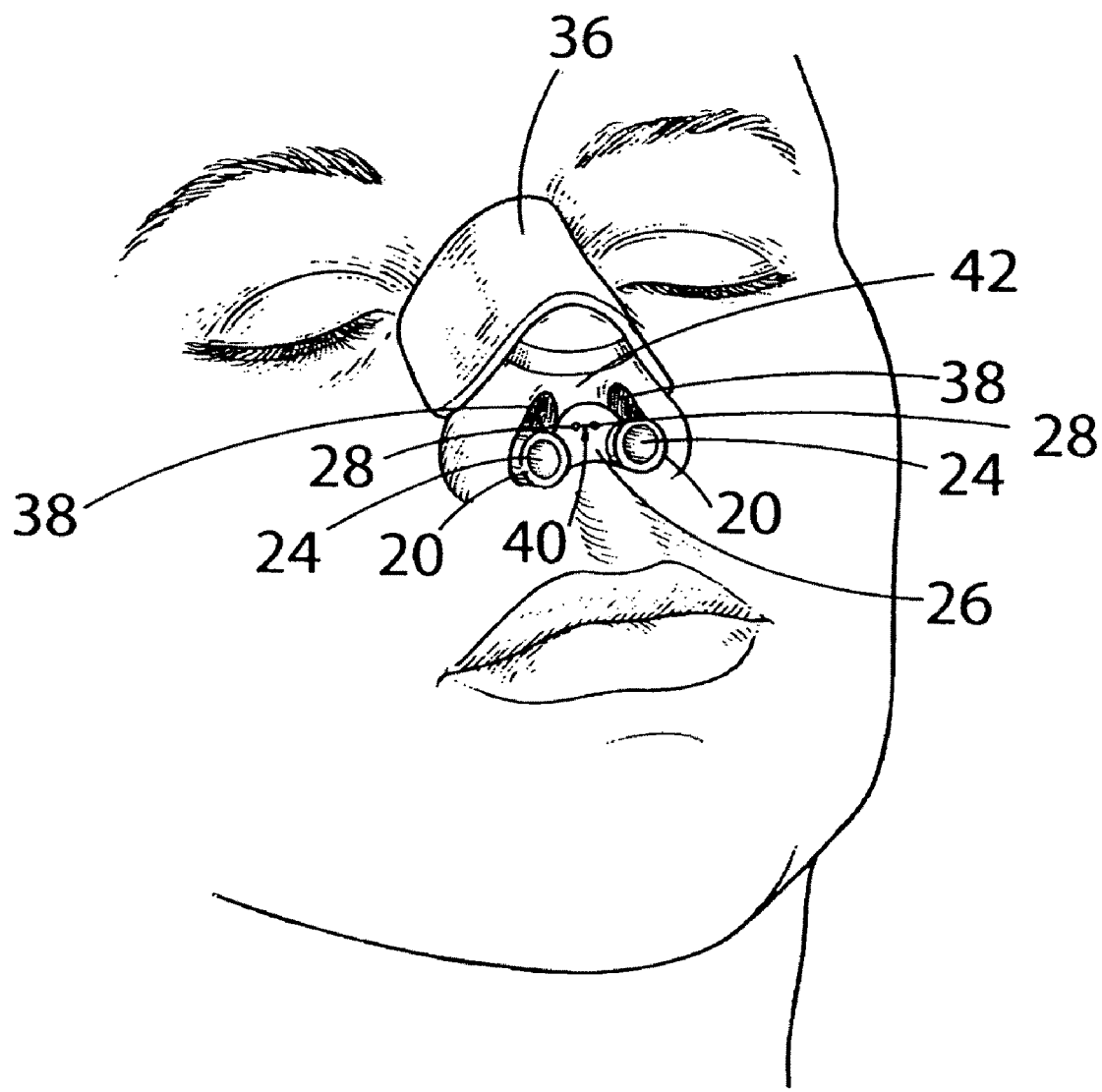
FIG. 4 is a perspective view of the post-operative medical device of FIG. 1 inserted into the nasal passages of a patient.

Referring now to FIGS. 1 to 3, one embodiment of a post-operative medical device 10 of the present invention is shown. In this embodiment, the medical device 10 is splintless. That is, the medical device is devoid of splints, where a splint is generally a device that is used to stabilize a repaired nasal septum. Although this embodiment of the medical device of the present invention is splintless and need not be used in conjunction with a splint to achieve its intended purpose, the medical device may, nonetheless, be used in conjunction with a splint, if the medical professional so chooses.

The embodiment of the medical device 10 shown in FIGS. 1 to 3 includes two tubular members 20, where each tubular member 20 has a plurality of graduations 22 and a slight curvature along its length. Each tubular member 20 has a proximal end 30, a distal end 32, and a lumen 24 that extends from the proximal end 30 to the distal end 32. The proximal end 30 of one tubular member 20 is connected to the proximal end 30 of the other tubular member 20 with a bridging member 26. Any suitable bridging member may be used to prevent extrusion of the tubular members from the nasal passages. For example, the bridging member may be a suture or a piece of plastic having any suitable shape.

As shown in FIGS. 1 and 2, the bridging member 26 is placed a distance d from the tip 34 of the proximal end 30. In this embodiment, the bridging member 26 contains a plurality of apertures 28 through which a suture may be passed to attach the bridging member 26 to a columella of a patient. In other embodiments, the bridging member is connected to a single tubular member adapted for insertion into one nasal passage.

Although in the embodiments shown in FIGS. 1 to 3 the tubular members 20 have a generally symmetrical, slightly curved, cylindrical configuration with a generally circular proximal tip 34, numerous other configurations are possible. For example, in some embodiments of the present invention, the tubular members of the medical device have a generally straight configuration with oblong proximal ends. Any tubular member configuration that fits comfortably within the nasal passages of a patient and permits sufficient airflow through the nasal passages may be used.

Figure 5:
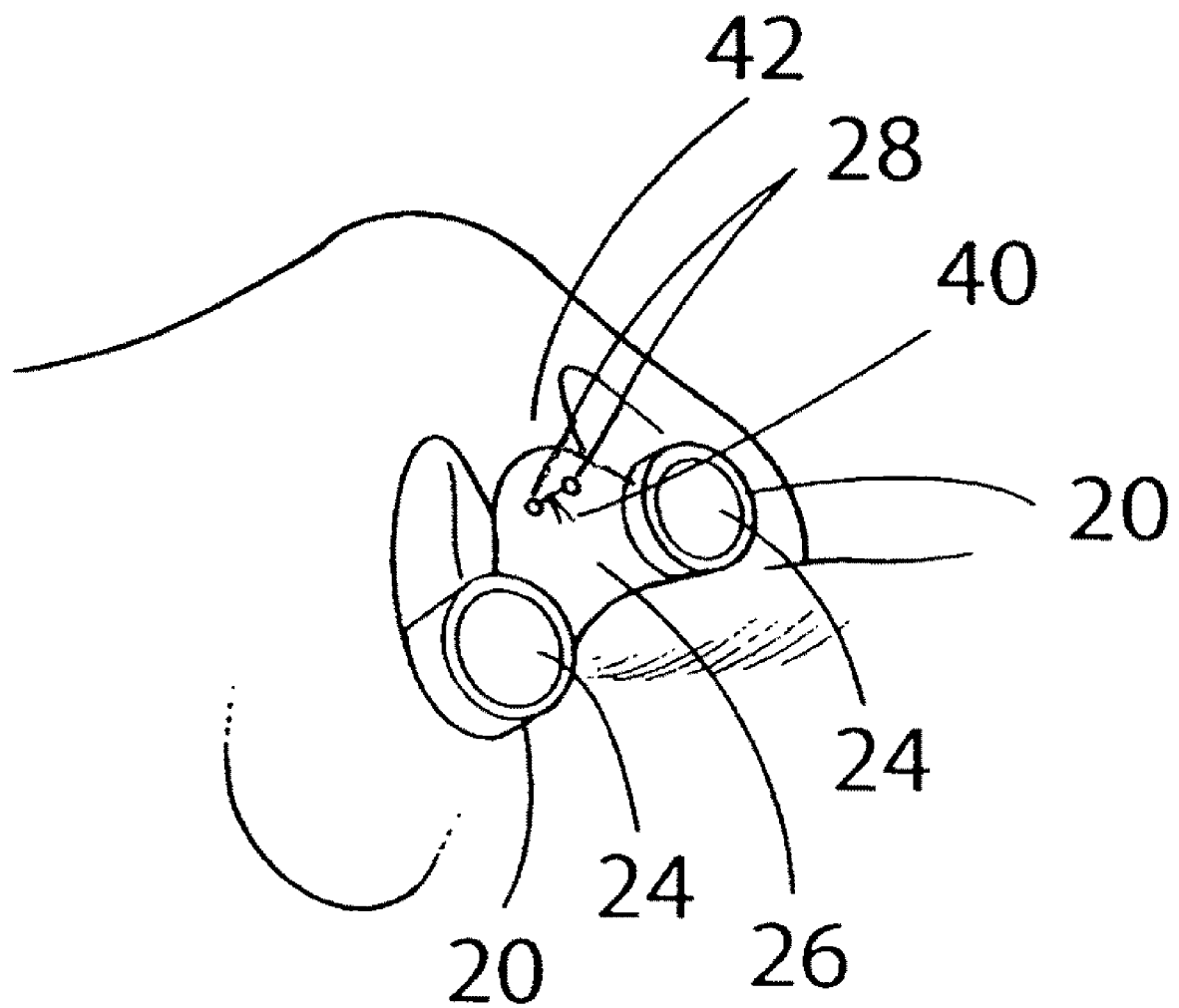
FIG. 5 is a magnified perspective view of one embodiment of the post-operative medical device of the present invention inserted into the nasal passages of a patient.
Figure 5A:
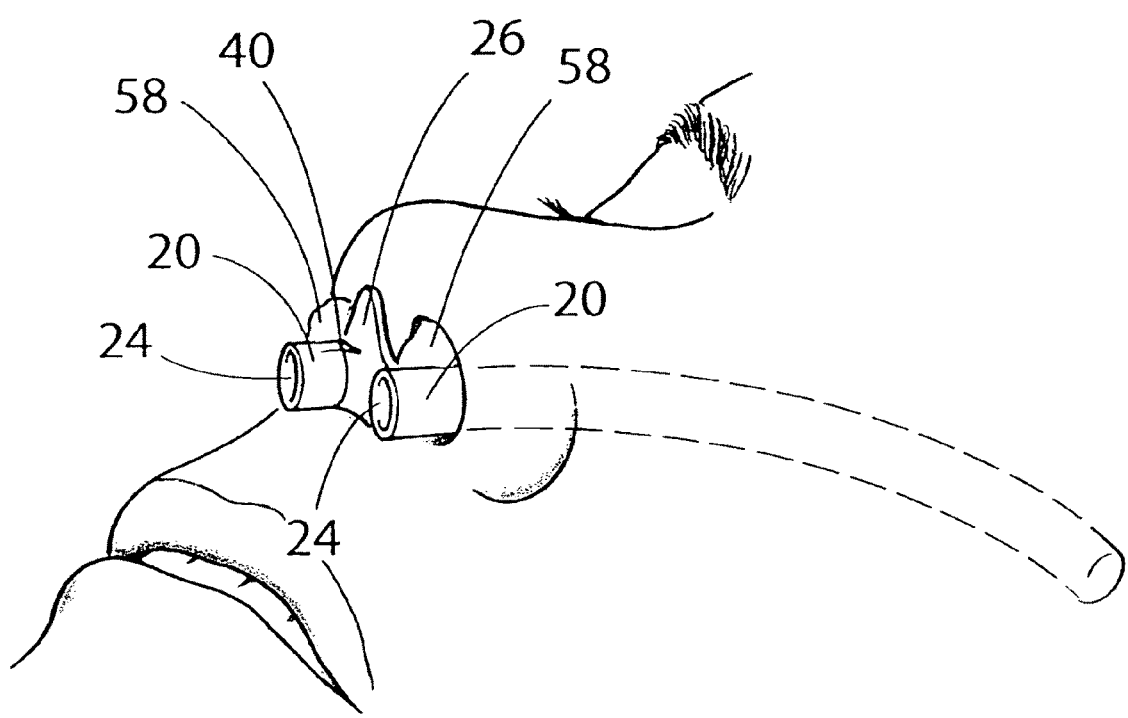
FIG. 5A is a perspective view of one embodiment of the post-operative medical device of the present invention after the insertion of packing material around the tubular members of the medical device.

The medical device 10 may be placed within a patient after nasal surgery, as shown in FIG. 4. As shown, each tubular member 20 is placed into the nostril openings 38 of the patient and through the nasal passages, as shown in more detail in FIG. 5. The bridging member 26 lies beneath the columella 42 of the patient and may be attached to the columella 42 with a suture 40 that passes through one or more apertures 28 in the bridging member 26, and the suture may be tied on the external side of the bridging member 26. In addition, an external nasal protector 36 may be applied to the top of a patient's nose following surgery, as shown in FIG. 4. Referring now to FIG. 5A, one embodiment of the post-operative medical device of the present invention is shown with packing material 58 placed within the nasal cavity of a patient near the tubular members 20 of the medical device.

Figure 6:
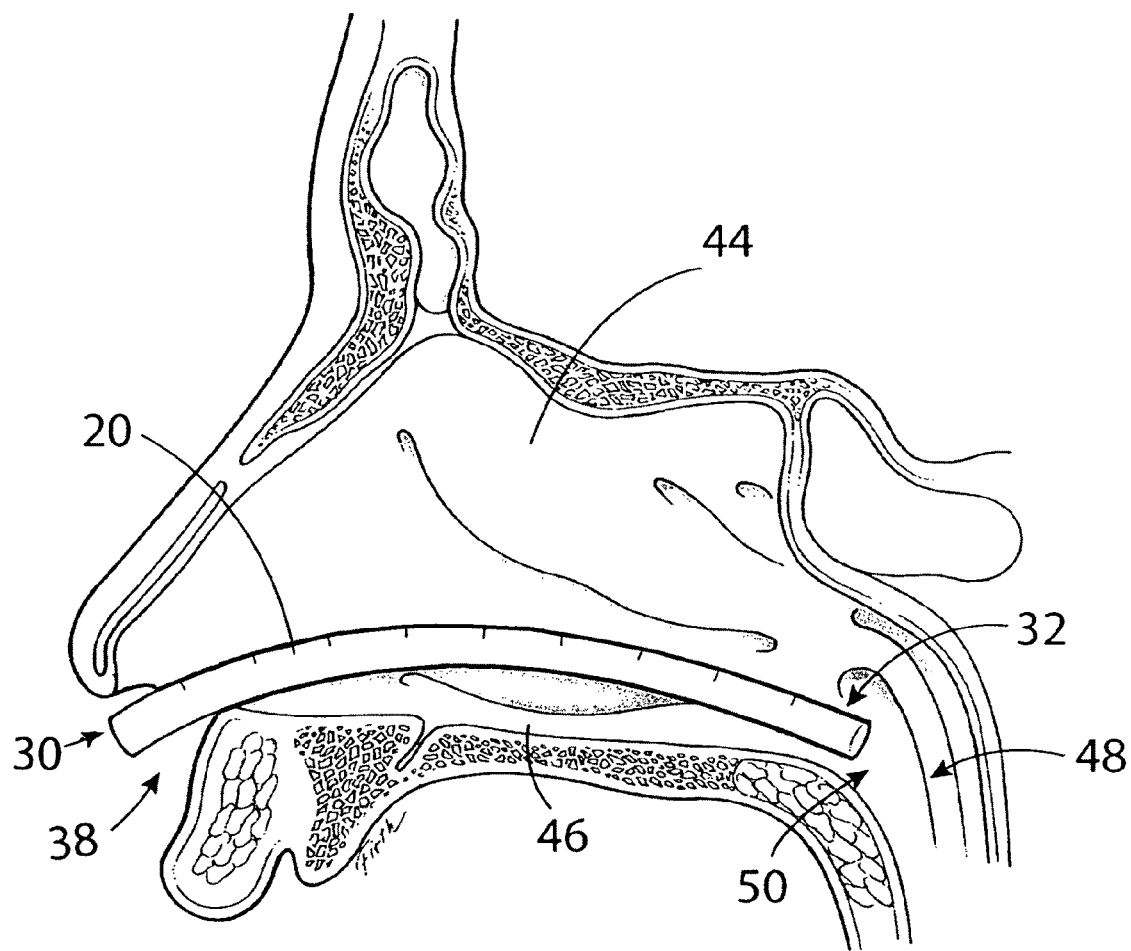
FIG. 6 is a sectional view of the nasal architecture of a patient illustrating the placement of a tubular member of one embodiment of a post-operative medical device of the present invention in a nasal passage of the patient.

The internal positioning of one embodiment of a tubular member 20 of a medical device of the present invention is shown in FIG. 6. As shown, the tubular member 20 protrudes from the nostril opening 38 and extends into the nasal cavity 44, lying near the floor 46 of the nasal cavity 44. The distal end 32 of the tubular member 20 extends to a position near the upper portion of the throat 48 and the back portion of the nasal cavity 50, beyond the area of the nasal cavity that ultimately will be filled with packing material. Air flows from the proximal end 30 of the tubular member 20 to the distal end 32 of the tubular member 20 and, via the throat, into the lungs of the patient.

The embodiments of the medical device of the present invention may have any suitable dimensions, so long as each tubular member of the medical device fits comfortably within the nasal passage of a patient without exerting excessive pressure on the inner walls of the nasal cavity. In some embodiments, each tubular member has an inner diameter of about 2 millimeters to about 6 millimeters and an outer diameter of about 4 millimeters to about 8 millimeters. In other embodiments, each tubular member has an inner diameter of about 3 millimeters to about 5 millimeters and an outer diameter of about 5 millimeters to about 7 millimeters. In still other embodiments, each tubular member has an inner diameter of about 4 millimeters and an outer diameter of about 6 millimeters.

Each tubular member of the medical device of the embodiments of the present invention may have any suitable length for positioning within a nasal passage of a patient. In certain embodiments, each tubular member has a length such that the tubular member protrudes slightly beyond the nostril opening of a patient, as shown in FIGS. 4 and 5, and extends rearwardly to a location near the back of the nasal cavity, as shown in FIG. 6. In some embodiments, each tubular member is adapted to be trimmed to the appropriate length. The appropriate length may be determined by the use of a suitable measuring device, including graduated markings on the medical device itself.

Any suitable materials may be used for the medical device of the present invention. In some embodiments, a soft and pliable medical grade silicon is used for both the tubular members and the bridging member. In other embodiments, a more rigid material is used. If desired, any or all portions of the medical device also may include a suitable coating.

In some embodiments of the present invention, the post-operative medical device includes three separate components: a first tubular member, a second tubular member, and a bridging member, where the components are connected to one another by one or more suitable connecting mechanisms. In other embodiments, the medical device is a single, integrally molded device. Such an embodiment eliminates the possibility of separation of the components during insertion or removal of the device or during the duration of residence of the device within the nasal passages of a patient.

In one embodiment of the present invention, a method for maintaining nasal passages open after nasal surgery, where the nasal passages are prone to obstruction by bodily fluids, is provided. In this embodiment, at least some of the bodily fluids are initially cleaned from the nasal passages after the nasal surgery. A post-operative medical device having a first tubular member and a second tubular member is provided, where the medical device is devoid of splints. The first tubular member has a first proximal end and a first distal end, and the second tubular member has a second proximal end and a second distal end. The first proximal end is connected to the second proximal end with a bridging member. The first distal end is inserted into a first nasal passage of a patient, and the second distal end is inserted into a second nasal passage of the patient. In this embodiment, the tubular members are simultaneously inserted into the nasal passages of the patient. In other embodiments, the tubular members are sequentially inserted into the nasal passages before the first and second proximal ends of the tubular members are connected with a bridging member. Packing may then be placed at least partially around each tubular member within the first and second nasal passages. In some embodiments, a suture is passed through apertures in the bridging member to stitch the bridging member to the columella of the patient.

In certain embodiments of the method of the present invention, the insertion of a tubular member into a nasal passage comprises inserting the tubular member into the nasal passage until the distal end of the tubular member contacts the upper portion of the throat, and then pulling the tubular member out of the nasal passage a small distance, such as a distance of about 1 to about 5 millimeters. Alternatively, a measuring device may be used to determine the length of the nasal floor before the tubular member is inserted into the nasal passage. The tubular member may then be trimmed at the distal end to the proper length, if necessary, and inserted into the nasal passage the proper distance. Graduations on the tubular member may facilitate this purpose. In certain embodiments, the tubular member protrudes from the nasal opening a small distance, such as about 1 to about 7 millimeters, about 2 to about 6 millimeters, or about 3 to about 5 millimeters. Such protrusion facilitates the cleaning of the tubular member by the patient.

The medical device may remain within the nasal passages of a patient for any suitable period of time. The device may remain within the nasal passages until the nasal architecture is sufficiently healed to permit removal of the packing material, as determined by the patient's physician. For example, the device may remain within the nasal passages of a patient for a period of about one to about five days. In some embodiments of the method of the present invention, the device is removed after about two days, three days, four days, or five days. The device may be removed in any suitable manner, including without limitation, by hand or by using an appropriate medical instrument.

Figure 7:
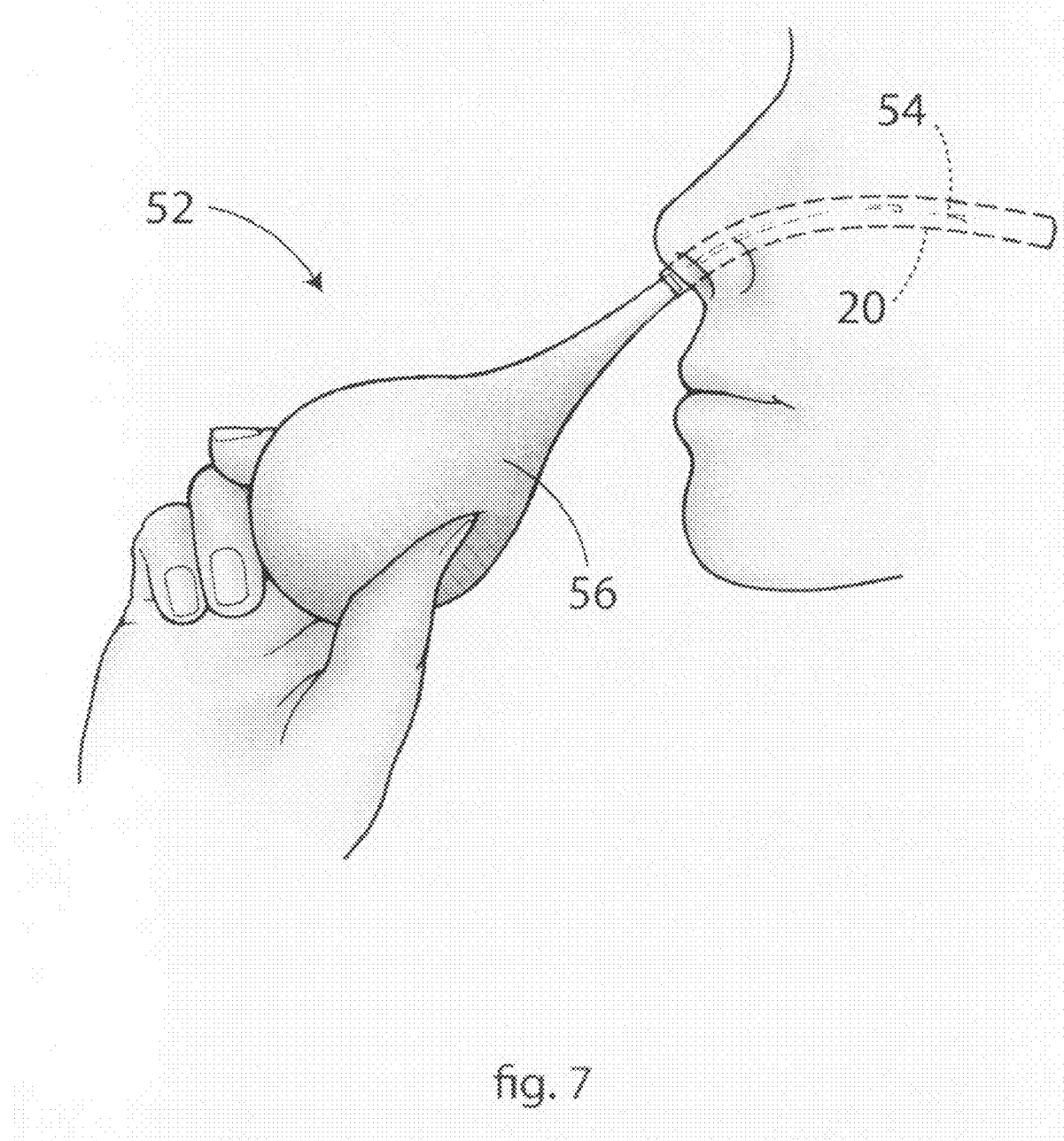
FIG. 7 is a perspective view illustrating the use of a device for cleansing a tubular member of one embodiment of a post-operative medical device of the present invention.

In certain embodiments of the method of the present invention, such as the embodiment illustrated in FIG. 7, a syringe 52 is used to clean each tubular member 20 by using water or another suitable fluid 54 to flush any obstructing material through the tubular member 20. The cleaning may be performed by either the patient or the physician by simply placing the syringe at least partially into the tubular member and squeezing the syringe 52 to release the fluid 54 and flush the obstructing material from the tubular member 20. Any suitable type of syringe or other cleaning device may be used. For example, a suction device, an elongated and flexible rod-like device adapted to be inserted into the tubular member, or a syringe 52 with a flexible bulb portion 56 may be used. The cleaning device may include an adapter to removably connect the cleaning device to each tubular member.

Any type of suitable packing material may used in this embodiment of the method of the present invention. Examples of suitable packing materials include, but are not limited to, polyvinyl alcohol expandable foam packing; petrolatum-impregnated gauze; absorbable, oxidized, regenerated cellulose knitted fabric; absorbable, oxidized, regenerated cellulose pledgets; cotton wadding; and non-adherent pads. In embodiments where non-adherent pads are used, the pad may be folded along the longitudinal axis of the pad before insertion of the pad into the nasal passage. Multiple pads may be used in this manner.

Figure 8:
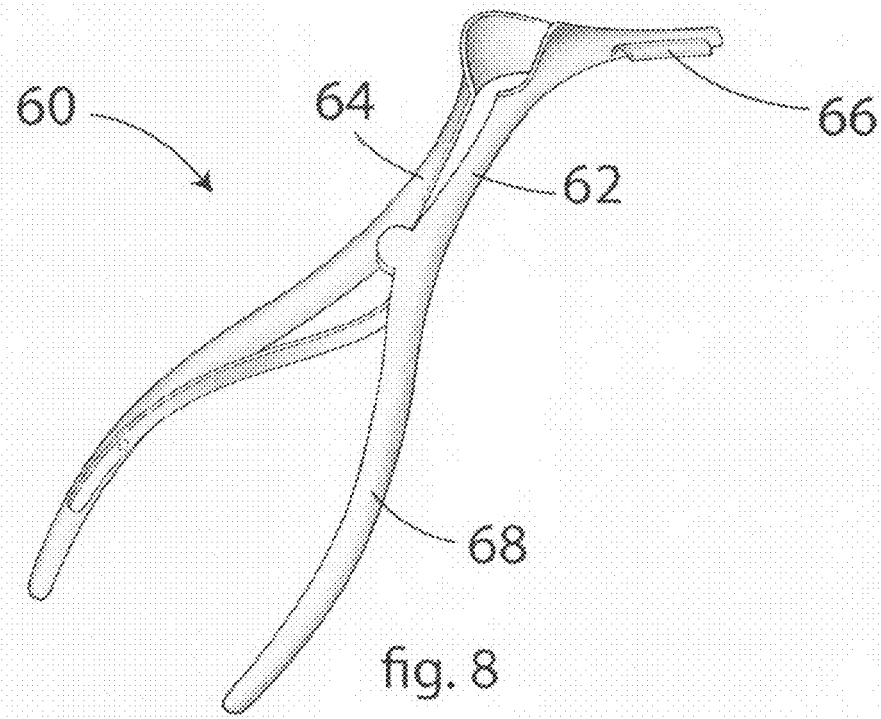
FIG. 8 is a perspective view of one embodiment of the specialized speculum of the present invention.
Figure 8A:
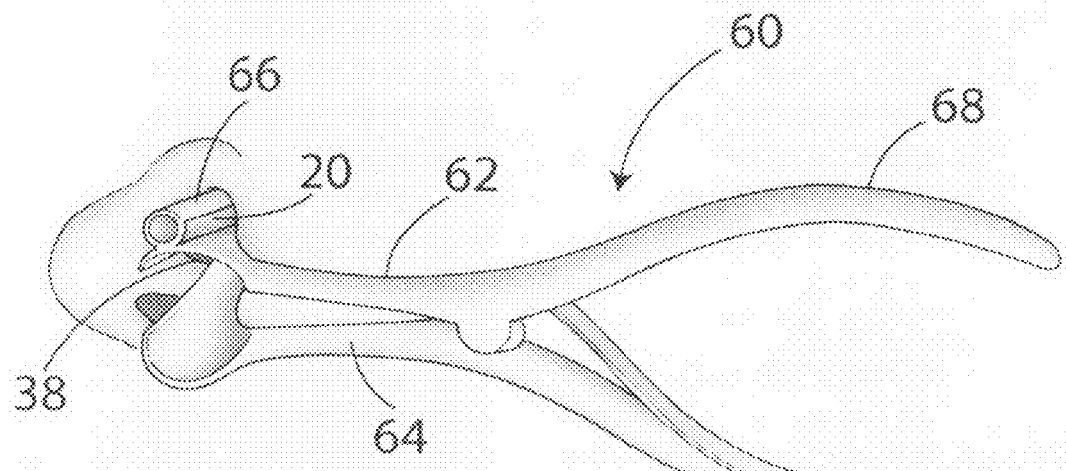
FIG. 8A is an illustration of one embodiment of the specialized speculum of the present invention inserted into a nostril opening of a patient.

To assist with the placement of packing material into the nasal cavity of a patient to at least partially surround the tubular member of the medical device, a specialized speculum may be used. One embodiment of such a speculum 60 is illustrated in FIG. 8. In this embodiment, the speculum has a handle 68, a first leg member 64, and a second leg member 62. The first leg member may have any shape suitable for insertion into the nasal passage of a patient and for application of pressure against the inner wall of the nasal cavity to temporarily expand the nostril opening 38, as shown in FIG. 8A, and increase the medical professional's visual and spatial access to the area surrounding a tubular member of a medical device, with minimal discomfort to the patient. In one embodiment, the first leg member 64 has a slightly curved or arc shape that generally conforms to the curvature of the nostril of the patient, and the second leg member 62 includes a tube engaging member 66 adapted to partially surround and/or mate with a tubular member 20 of a post-operative medical device. The tube engaging member 66 may be integral with the second leg member 62 of the specialized speculum 60 or it may be added as a retrofit to a typical speculum to create a specialized speculum.

Figure 9:
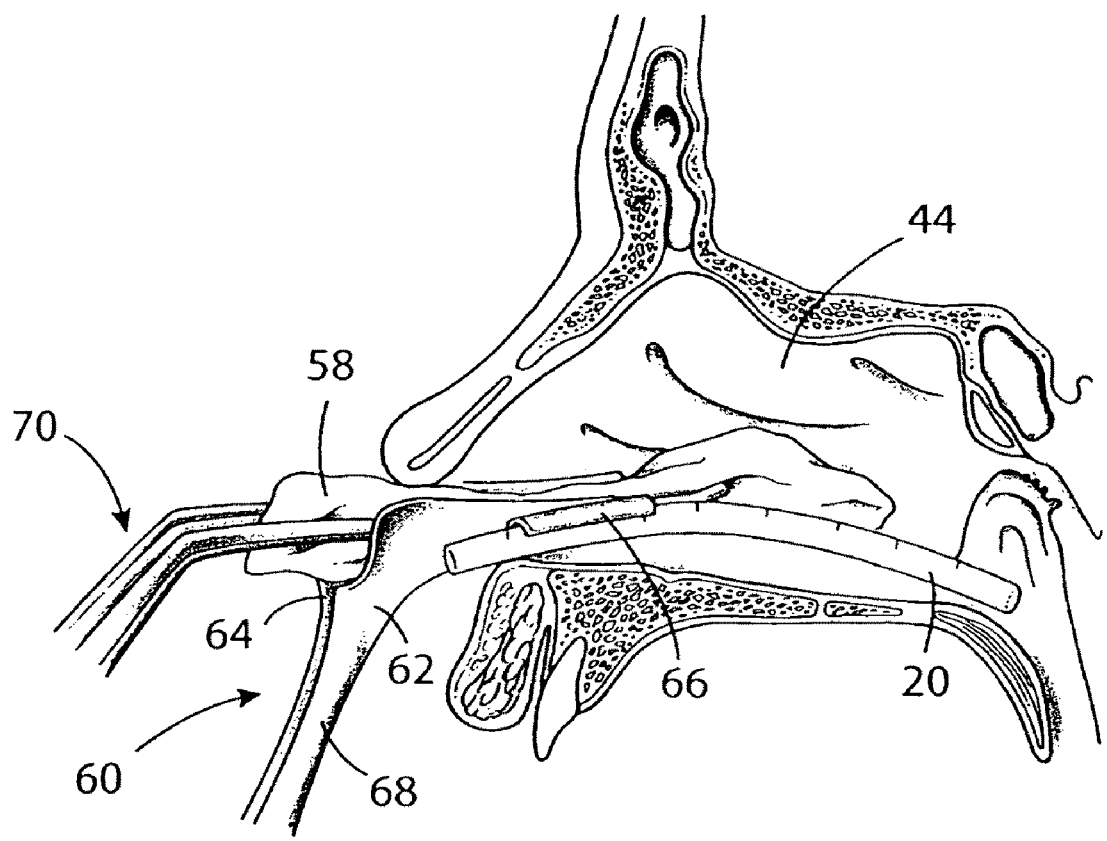
FIG. 9 is an illustration of the placement of packing material into the nasal cavity of a patient using one embodiment of a specialized speculum of the present invention.

In operation, as shown in FIG. 9, after insertion of a tubular member 20 into the nasal passage of a patient following surgery, the specialized speculum 60 may be inserted into the nasal passage in a first position. The speculum may then be moved to a second position that results in the tube engaging member 66 partially surrounding and mating with the external curvature of the tubular member 20 of the post-operative medical device, thereby stabilizing the tubular member 20 and exerting sufficient pressure against the tubular member 20 to permit easy placement of packing material 58 between the tubular member 20 and the inner wall of the nasal cavity 44 of the patient. The packing material 58 may be inserted using forceps 70, as shown in FIG. 9, or any other suitable instrument.

The specialized speculum 60 may be made from any suitable material for insertion into the nasal passage of a patient. For example, the specialized speculum 60 may be made from a suitable metal such as a sterilizable stainless steel. Alternatively, the specialized speculum may be made from a less costly, single-use material such as a suitable plastic.

In some embodiments of the present invention, a kit is provided, where the kit includes a post-operative medical device and a specialized speculum, such as the speculum described above. In certain embodiments, the specialized speculum is a single-use speculum. In some embodiments, the kit also may include other components useful following nasal surgery, such as a suitable packing material.

The embodiments of the present invention may be useful for at least the surgical specialties relating to head and neck (ear, nose, and throat) surgery and plastic surgery. Additionally, individuals practicing oral surgery, a dental specialty whose sphere includes some nasal surgery, may avail themselves of the advantages of the present invention, as may other medical professionals.

While the invention has been described with reference to particular embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for maintaining nasal passages open after nasal surgery, wherein the nasal passages are prone to obstruction by bodily fluids, the method comprising:
   (a) initially cleaning at least some of the bodily fluids from the nasal passages after the nasal surgery;
   (b) providing a post-operative device comprising a first tubular member comprising a first proximal end and a first distal end, and a second tubular member comprising a second proximal end and a second distal end, wherein the first proximal end is connected to the second proximal end with a bridging member, and the post-operative device is splintless;
   (c) inserting the first distal end and the second distal end into nostril openings and through the nasal passages to a location where the first proximal end and the second proximal end each protrude beyond the nostril openings of a patient; and
   (d) positioning the first distal end and the second distal end at an entrance to a patient's throat.

2. The method of claim 1 further comprising securing the bridging member to a columella of a patient.

3. The method of claim 2 wherein the bridging member is secured to the columella by suturing the bridging member to the columella.

4. The method of claim 3 wherein the bridging member comprises an aperture and the bridging member is sutured to the columella by passing a suture through the aperture and the columella.

5. The method of claim 1 wherein the first proximal end is connected to the second proximal end after the first distal end and the second distal end are inserted into the nasal passages.

6. The method of claim 1 wherein the first proximal end is connected to the second proximal end before the first distal end and the second distal end are inserted into the nasal passages.

7. The method of claim 1 wherein the method further comprising cleaning each tubular member with a syringe comprising a fluid.

8. The method of claim 7 wherein the step of cleaning each tubular member with a syringe further comprises using an adapter to removably connect the syringe to each tubular member.

9. The method of claim 1 wherein each tubular member is slightly curved.

10. The method of claim 9 wherein each tubular member has an inner diameter of about 4 millimeters and an outer diameter of about 6 millimeters.

11. The method of claim 1 further comprising removing the post-operative device from the nasal passages at least two days after insertion.

12. The method of claim 1 further comprising using a speculum to facilitate at least partially surrounding each tubular member with packing material.

13. The method of claim 1, further comprising at least partially surrounding each tubular member with packing material so that the first distal end and the second distal end extend distal to the packing material in the nasal passages.

14. The method of claim 13, comprising inserting the first distal end and the second distal end into the nasal passages until the first and second distal ends contact an upper portion of a patient's throat and withdrawing the first and second distal ends away from contact with the throat.

15. The method of claim 14, comprising withdrawing the first and second distal ends about 1 to about 5 mm away from the throat.

16. The method of claim 1, further comprising inserting a cleaning device into an opening in the proximal end of the first tubular member and flushing the first tubular member with a fluid.

17. The method of claim 1, comprising connecting the first tubular member and the second tubular member with the bridging member so that the bridging member connects the first tubular member and second tubular member without covering an opening in the first proximal end and an opening in the second proximal end.

18. The method of claim 1, further comprising providing a medical device for holding the first tubular member, the medical device having a first position and a second position within the nasal passage.

19. A method for maintaining nasal passages open after nasal surgery, wherein the nasal passages are prone to obstruction by bodily fluids, the method comprising:
   (a) initially cleaning at least some of the bodily fluids from the nasal passages after the nasal surgery;
   (b) providing a post-operative device comprising a first tubular member comprising a first proximal end and a first distal end, and a second tubular member comprising a second proximal end and a second distal end, wherein the first proximal end is connected to the second proximal end with a bridging member, and the post-operative device is splintless;
   (c) inserting the first distal end and the second distal end into nostril openings and through the nasal passages to a location where the first proximal end and the second proximal end each protrude beyond a nostril opening of a patient;

(d) positioning the first distal end and the second distal end at an entrance to a patient's throat;

(e) securing the bridging member to the columella by suturing the bridging member to the columella; and (f) trimming the first distal end and the second distal end prior to securing the post-operative device.

20. The method of claim 19, further comprising providing markings on the first and second tubular members to determine an appropriate length of the first and second tubular members.

* * * * *